(12) United States Patent
Sanganabhatla et al.

(10) Patent No.: US 7,763,645 B2
(45) Date of Patent: Jul. 27, 2010

(54) CARVEDILOL DIHYDROGEN PHOSPHATE MONOHYDRATE

(75) Inventors: Shankar Sanganabhatla, Navi Mumbai (IN); Sunanda Manoj, Mumbai (IN); Ramanarasimha Moorthy Koduru, Mumbai (IN)

(73) Assignee: Wanbury Limited, Navi-Mumbai (IN)

( * ) Notice: Subject to any disclaimer, the term of this patent is extended or adjusted under 35 U.S.C. 154(b) by 106 days.

(21) Appl. No.: 12/247,653

(22) Filed: Oct. 8, 2008

(65) Prior Publication Data
US 2009/0291997 A1 Nov. 26, 2009

(30) Foreign Application Priority Data
May 23, 2008 (IN) .................. 1094/MUM/2008

(51) Int. Cl.
*A61K 31/403* (2006.01)
*C07D 209/88* (2006.01)

(52) U.S. Cl. ...................... 514/411; 548/440
(58) Field of Classification Search ................ None
See application file for complete search history.

(56) References Cited

U.S. PATENT DOCUMENTS

| 4,503,067 A | 3/1985 | Wiedemann et al. |
| 7,268,156 B2 | 9/2007 | Brook et al. |
| 2005/0169994 A1 * | 8/2005 | Burke et al. ............... 424/469 |
| 2005/0277689 A1 | 12/2005 | Brook et al. |

FOREIGN PATENT DOCUMENTS

| WO | WO2007144900 A2 | 12/2007 |
| WO | WO2008002683 A2 | 1/2008 |

OTHER PUBLICATIONS

U.S. Appl. No. 11/936,634, Sanganabhatla et al.
Packer M et al., Effect of carvedilol on the morbidity of patients . . . , . Circulation. 2002; vol. 106(No. 17):pp. 2194-2199.

* cited by examiner

*Primary Examiner*—Kamal A Saeed
*Assistant Examiner*—Michael Barker
(74) *Attorney, Agent, or Firm*—Proteus Patent Practice LLC; Henry E. Auer

(57) ABSTRACT

Disclosed herein is crystalline carvedilol dihydrogen phosphate monohydrate having high aqueous solubility and the process for preparation thereof. The invention further discloses methods for treating hypertension, congestive heart failure and angina in a mammal, using pharmaceutical compositions comprising the compound of invention.

24 Claims, 4 Drawing Sheets

CARVEDILOL DIHYDROGEN PHOSPHATE MONOHYDRATE

FIELD OF THE INVENTION

The present invention is drawn to a novel pharmaceutical agent useful in the treatment of cardiovascular disease. More specifically the invention relates to crystalline carvedilol phosphate monohydrate, methods of its preparation, and methods of use in treatment of cardiovascular diseases.

TECHNICAL FIELD

The present invention relates to a novel crystalline monohydrate phosphate salt of 1-(9H-carbazol-4-yloxy)-3-[[2-(2-methoxyphenoxy)ethyl]amino]-propan-2-ol, (carvedilol phosphate monohydrate) of formula (I).

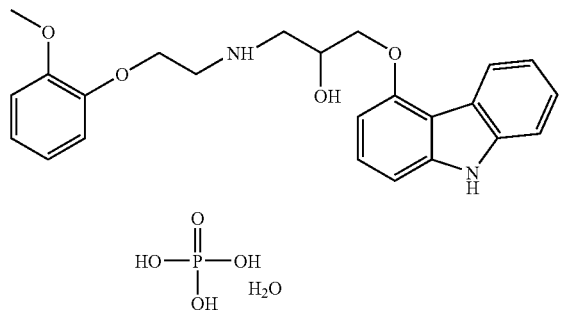

Further, the invention relates to a process for preparation of monohydrate salt of carvedilol using various phosphate forming reagents such as phosphoric acid, phosphorus pentoxide, polyphosphoric acid, dipotassium hydrogen phosphate, ammonium dihydrogen ortho phosphate, and sodium dihydrogen ortho phosphate in solvents selected from acetonitrile, acetone, isopropyl alcohol and tetrahydrofuran and water.

BACKGROUND OF THE INVENTION

Carvedilol, the first beta blocker labeled in the United States for the treatment of heart failure, has been shown to improve left ventricular ejection fraction and may reduce mortality. Carvedilol is chemically known as 1-(9H-carbazol-4yloxy)-3-[[2-(2-methoxyphenoxy)-ethyl]amino]-propan-2-ol, which has the following structure (II).

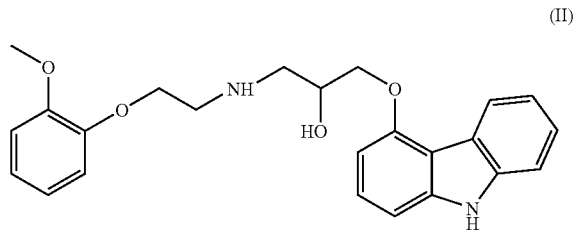

Carvedilol is disclosed in U.S. Pat. No. 4,503,067 to Wiedemann et al. Carvedilol is indicated in the management of congestive heart failure (CHF), as an adjunct to conventional treatments (ACE inhibitors and diuretics). Currently, carvedilol is used for treating patients suffering with hypertension, congestive heart failure and angina. The use of carvedilol has been shown to provide additional morbidity and mortality benefits in CHF (Packer M, Fowler M B, Roecker E B, et al. Effect of carvedilol on the morbidity of patients with severe chronic heart failure: results of the carvedilol prospective randomized cumulative survival (COPERNICUS) study. Circulation. 2002;106(17):2194-9. *PMID* 12390947

The patent application publication US20050277689 A1 and U.S. Pat. No. 7,268,156 both describe crystalline forms of carvedilol dihydrogen phosphate including the hemihydrate, the dihydrate and certain solvates thereof. The publications state that the various carvedilol phosphate forms exhibit high aqueous solubility. Carvedilol dihydrogen phosphate hemihydrate is disclosed to be synthesized by reacting carvedilol with phosphoric acid in aqueous acetone. Crystals of the product are obtained by seeding with carvedilol dihydrogen phosphate. The publications state that the corresponding dihydrate is obtained by slurrying the hemihydrate in an acetone/water mixture for several days, or by distilling off the acetone to crystallize the product in the residual solvent.

The PCT patent publication WO2008002683A2 describes amorphous carvedilol phosphate (in which carvedilol and phosphate are defined as being present in a molar ratio of about 3:1), amorphous carvedilol hydrogen phosphate (in which carvedilol and phosphoric acid are defined as being present in a molar ratio of about 2:1), amorphous carvedilol dihydrogen phosphate (in which carvedilol and phosphate are defined as being present in a molar ratio of about 1:1), crystalline carvedilol dihydrogen phosphate as well as numerous exemplary processes for preparation of the same. The different forms of carvedilol dihydrogen phosphate disclosed in WO2008002683A2 are either the hemihydrate or the dihydrate. Methods of synthesizing carvedilol dihydrogen phosphate are disclosed generally as including combining carvedilol, phosphoric acid and an essentially nonaqueous organic solvent, and precipitating carvedilol dihydrogen phosphate from the reaction mixture.

WO2008002683A2 provides characterization data such as x-ray diffraction (XRD), differential scanning calorimetry (DSC) and thermo gravimetric analysis (TGA) for the claimed compounds.

The PCT patent publication WO2007144900A2 claims crystalline carvedilol dihydrogen phosphate sesquihydrate having moisture content between 4 to 7%, preferably to 4.5 to 6.0%. Processes for preparing this composition are disclosed.

There is a need for improved carvedilol compositions displaying high purity, high stability, and high bioavailability in a mammal after oral administration. The latter need includes the need for a composition having high solubility in environments of relatively neutral pH or higher such as may be encountered in the digestive tract of the small intestine of the mammal, where the solubility of carvedilol is low. There further is a need for a pharmaceutical composition including a carvedilol salt that provides rapid dissolution after oral administration, and high bioavailability of active carvedilol.

The present disclosure addresses these and related needs. The presently disclosed composition and methods are directed to provide stable and highly water soluble novel crystalline carvedilol dihydrogen phosphate monohydrate salt of formula I. The invention also directed to convenient, robust and rugged processes for the preparation of the subject matter of the present invention

SUMMARY OF THE INVENTION

In one aspect, crystalline carvedilol dihydrogen phosphate monohydrate is disclosed. The product is characterized by the scattering peaks in its x-ray diffraction pattern, by its differential scanning calorimetric thermogram, and by assay of its water content.

In a second aspect a process for the preparation of carvedilol dihydrogen phosphate monohydrate is disclosed. The process includes process steps of
 a. preparing a slurry of carvedilol in water;
 b. contacting the slurried carvedilol with a composition comprising a source of phosphate at a temperature from about 25 to about 55° C., thereby generating a phosphate salt of carvedilol in water;
 c. adding a water-miscible organic solvent to the aqueous carvedilol phosphate salt at a temperature from about 25 to about 55° C.; and
 d. cooling the aqueous-organic mixture and isolating solid carvedilol dihydrogen phosphate monohydrate salt from the mixture.

In various embodiments of the process, the source of phosphate is selected from the group consisting of phosphoric acid, phosphorus pentoxide, polyphosphoric acid, dipotassium hydrogen phosphate, ammonium dihydrogen ortho phosphate, sodium dihydrogen ortho phosphate, and a mixture of any two or more of them. Furthermore, in various other embodiments a variety of water-miscible organic solvents are disclosed for use in this process. In still additional embodiments of the process the ratio of water:organic solvent, expressed as volume:volume, ranges from 1:1 to 5:1.

In an additional aspect, a pharmaceutical composition that includes carvedilol dihydrogen phosphate monohydrate and a pharmaceutical carrier is disclosed.

In still a further aspect, use of crystalline carvedilol dihydrogen phosphate monohydrate for the preparation of a medicament useful for treating a subject suffering from, or at risk of developing, hypertension, congestive heart failure or angina.

In yet an additional aspect, a method is disclosed for treating a cardiovascular disease in a mammal. The method includes administering to the mammal a therapeutically effective amount of a pharmaceutical composition comprising carvedilol dihydrogen phosphate monohydrate. In various embodiments, the cardiovascular disease is one or more of hypertension, congestive heart failure and angina. In another embodiment the mammal is a human.

DETAILED DESCRIPTION OF THE INVENTION

Figure 1:
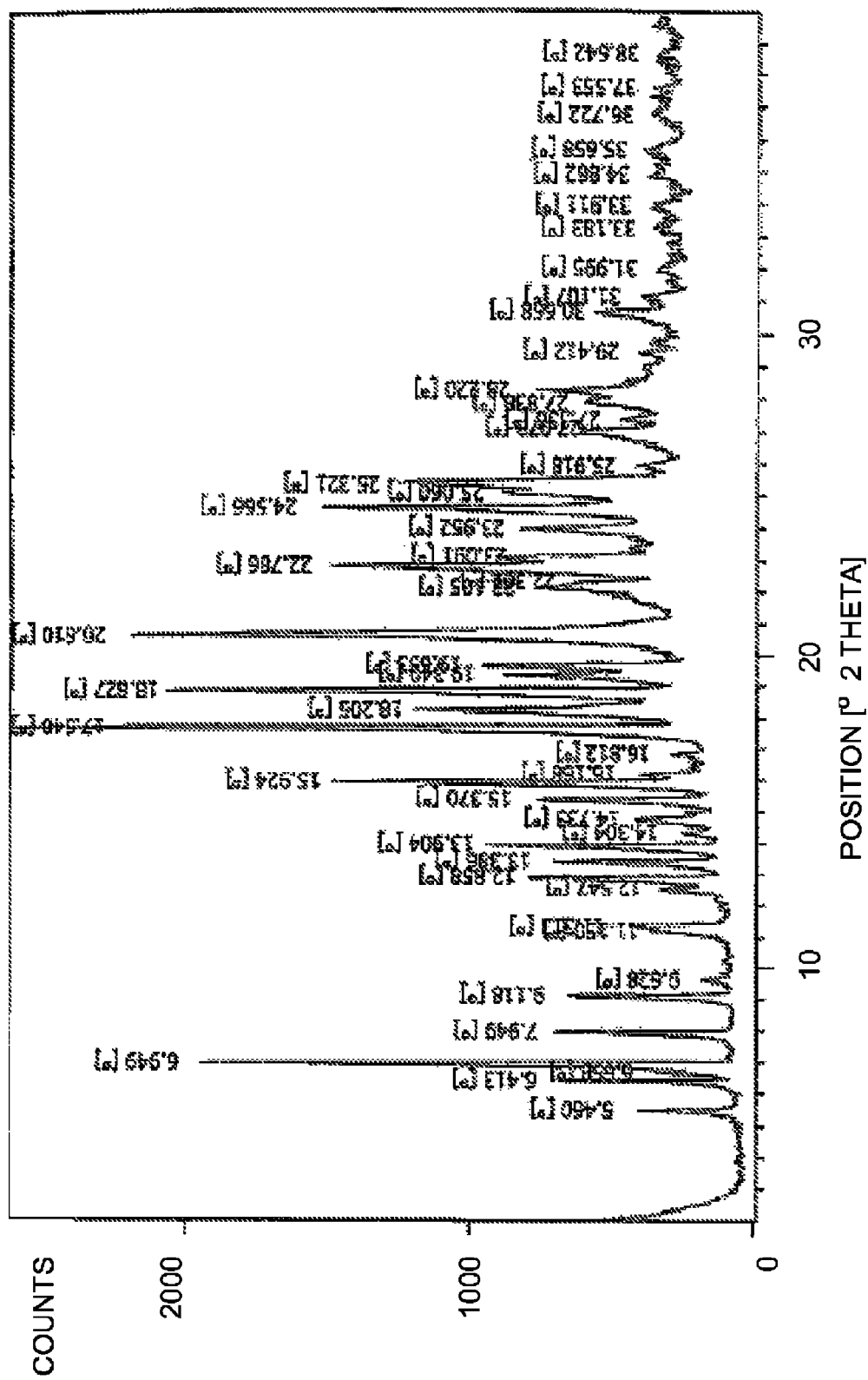
FIG. 1 presents an X-ray powder diffractogram for carvedilol dihydrogen phosphate monohydrate.

This disclosure provides crystalline carvedilol dihydrogen phosphate monohydrate. The inventors believe this composition has not previously been reported in the art. The water content confirming that the composition is carvedilol dihydrogen phosphate monohydrate was assessed by Karl Fisher moisture analysis and proton amplitude in the $^1$H NMR spectrum, as set forth in detail below. This composition has high purity, and is highly soluble under conditions that model pharmaceutical administration to a subject, thus assuring high bioavailability in a subject to whom the composition may be administered.

The disclosure additionally provides a novel process for the preparation of carvedilol dihydrogen phosphate monohydrate, rather than previously known carvedilol dihydrogen phosphate compositions, with high yields and high purity. The process of the present invention is simple to operate, affords a high yield, and is easily scalable to industrial production.

In broad conception the preparation method includes a small number of process steps.

First, a slurry of carvedilol in water is made. The slurry is stirred at an elevated temperature for a short period of time. In various embodiments the temperature of the slurry is in the range of 25-60° C., or is in the range from 30-55° C., or is in the range from 30-45° C., or is in the range from 30-35° C. In certain other embodiments the temperature may be maintained at lower temperature in order to counteract any exothermic processes that may occur in this or the next step. In various embodiments the slurry is stirred for at least 5 min., and for about 60 min. or less, or for about 30 min. or less, or for about 15 min. or less.

Second, a 1:1 salt of carvedilol and phosphate is generated by adding a suitable source of phosphate to the slurry. In various embodiments, the source of phosphate is selected from the group consisting of phosphoric acid, phosphorous pentoxide, polyphosphoric acid, dipotassium hydrogen phosphate, ammonium dihydrogen ortho phosphate or sodium dihydrogen ortho phosphate. Equivalent sources of phosphate known to a worker of skill in the field of the invention may also be used in this step without exceeding the scope of this disclosure. Optionally, if necessary a mineral acid may be added to adjust the pH to a range of about 4-5. In various embodiments the mixture is stirred in the temperature range of 25-60° C., or in the range from 30-55° C., or in the range from 50-55° C., or in the range from 30-45° C., or in the range from 40-45° C., or in the range from 30-35° C. The mixture is stirred for a further period of time of at least about 5 min. and for about 90 min. or less, or for about 60 min. or less, or for about 30 min. or less. Use of phosphate forming reagents such as enumerated herein has been disclosed in co-pending U.S. application Ser. No. 11/936,634 filed Nov. 7, 2007.

Third, a water-miscible organic solvent is added to carvedilol phosphate salt solution. In various embodiments the temperature of the mixture is maintained in the range of 25-60° C., or in the range from 50-55° C., or in the range from 30-55° C., or in the range from 30-45° C., or in the range from 30-35° C. In certain embodiments the mixture is first stirred with heating to about 50-55° C. for about 1 hr, or about 2 hr, or about 3 hr; then cooled back to about 30-35° C. for further stirring for an extended time of about 36 hr. or less, or for about 24 hr. or less, or for about 18 hr. or less. In various embodiments the organic solvent is selected from the group consisting of acetonitrile, tetrahydrofuran, dioxane, ethanol, n-propanol, isopropanol, and acetone. Equivalent water-miscible organic solvents known to a worker of skill in the field of the invention may also be employed without exceeding the scope of the invention. In various embodiments the ratio of water:organic solvent, expressed as volume:volume, may range from 1:1 to 5:1; in various additional embodiments the ratio may range from about 1.2:1 to about 1.5:1; in various other embodiments the ratio may range from about 4:1 to about 5:1, and in still further embodiments the ratio may vary from about 4.5:1 to about 4.8:1.

Fourth, the resulting aqueous-organic mixture is cooled to a temperature in the range of about 0-15° C., or in various embodiments to a temperature range of about 5-10° C. The mixture is held at this temperature for a time sufficient to crystallize carvedilol dihydrogen phosphate monohydrate. The product crystallizes from the mixture without the use of seed crystals. The crystals are harvested, washed with water or a mixed water-organic solvent approximating the composition of the reaction mixture, then dried to constant weight.

As used herein, the term "water content" refers to the content of water based upon the Karl Fisher assay for determining water content, upon thermogravimetric analysis (TGA) or upon the Loss on Drying method (the "LOD" method) as described in UPS 29-NF 24, official Aug. 1, 2006, Physical Test and Determinations, or in Pharmacopoeia Forum, Vol. 24, No. 1, p. 5438 (January-February 1998). All percentages herein are by weight unless otherwise indicated.

Based on molecular stoichiometry it is understood that the term "dihydrate" when used in reference to carvedilol dihydrogen phosphate describes carvedilol dihydrogen phosphate having a water content of between about 4.7-6.9% wt/wt. Those skilled in the art will also understand that the term "hemihydrate" when used in reference to carvedilol dihydrogen phosphate describes carvedilol dihydrogen phosphate having a water content of about 1.7-2.0% wt/wt.

The carvedilol dihydrogen phosphate monohydrate prepared by the present processes is dried till constant weight for 4-10 hours at 40-45° C. under vacuum to obtain carvedilol dihydrogen phosphate monohydrate having bound water content in the range of 3.0-4.0% wt/wt; the theoretical moisture content for carvedilol dihydrogen phosphate monohydrate is 3.54% wt/wt. Further, the bound water content was removed by drying the material at 110° C. till the moisture content below 0.5%. The original moisture content was regained after about 10-15 hours when exposed to 75% relative humidity at 37° C. (in air). These findings confirm that the monohydrate salt of carvedilol dihydrogen phosphate is stable and does not convert into the dihydrate or hemihydrate form under these conditions.

The carvedilol dihydrogen phosphate monohydrate synthesized by the processes disclosed herein are distinguished from other carvedilol dihydrogen phosphate hydrates, and from other carvedilol phosphate compositions, using various characterization or identification techniques. These include $^1$H nuclear magnetic resonance (NMR), Fourier transform infrared spectroscopy (FTIR), X-ray powder diffraction, and differential scanning calorimetry (DSC). Results are disclosed below, including in the Examples.

Based on the above, the invention further provides pharmaceutical compositions comprising carvedilol phosphate monohydrate together with pharmaceutically acceptable carrier/carriers. These carriers are added in the composition for a variety of purposes.

The carvedilol phosphate monohydrate of the present invention can be used in pharmaceutical preparations as the same is having high aqueous stability. The pharmaceutical preparations can be selected from various dosage forms such as solid dosage form like tablets, capsules, pellets, powders soft gelatin capsules, and the like and oral liquids. Various embodiments include dosage forms suitable for oral administration. The tablets can be prepared as conventional dosage forms such as immediate release, sustained release, modified release or controlled release.

The pharmaceutical compositions can be prepared using conventional techniques well known in the art.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in textbooks such as Remington's Pharmaceutical Sciences, Gennaro A R (Ed.) 20$^{th}$ edition (2000) Williams & Wilkins PA, USA, and Wilson and Gisvold's Textbook of Organic Medicinal and Pharmaceutical Chemistry, by Delgado and Remers, Lippincott-Raven., which are incorporated herein by reference.

Oral compositions generally include carvedilol dihydrogen phosphate monohydrate and one or more inert diluents or edible carriers that have been determined to pharmaceutically acceptable. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide. The compounds and/or pharmaceutical compositions can also include, by way of nonlimiting example, suitable adjuvants, carriers, excipients, or stabilizers, etc. and can be in solid or liquid form such as, tablets, capsules, powders, solutions, suspensions, or emulsions, etc.

According other embodiments disclosed herein, methods for treating hypertension, congestive heart failure and angina in mammals are disclosed, wherein said methods comprise administering therapeutically effective amounts of carvedilol dihydrogen phosphate monohydrate of the present invention or pharmaceutical compositions comprising the same. The compound of the present invention can also be administered optionally with other active agents depending on the disease conditions.

According to another embodiment, the invention provides use of crystalline Carvedilol phosphate monohydrate in pharmaceutical preparations.

"Therapeutically effective amount" means the amount of a crystalline form that, when administered to a patient for treating a disease or other undesirable medical condition, is sufficient to have a beneficial effect with respect to that disease or condition.

The quantity of the compound used in pharmaceutical compositions of the present invention will vary depending upon the body weight of the patient and the mode of administration and can be of any effective amount to achieve the desired therapeutic effect.

A worker of skill in the field of this disclosure understands how to determine a therapeutically effective amount to be applied in the treatment of a pathology such as cardiovascular disease. Such understanding includes a wide familiarity with in vitro and preclinical in vivo studies carried out in the development of various carvedilol phosphate agents. The understanding further profits from broad familiarity with properties of various pharmaceutical compositions, and the ways in which they affect bioavailability of an active agent incorporated therein. The understanding further benefits from close monitoring of therapeutic effects obtained with a population of human subjects treated according to the instantly disclosed methods.

Broadly, a pharmaceutical composition containing carvedilol dihydrogen phosphate monohydrate intended for systemic application, such as by oral dosing, may contain the active agent in a range, by way of nonlimiting example, from about 1 µg/kg of body weight or even less to about 100 mg/kg or even more, or a range from about 5 µg/kg of body weight to about 50 mg/kg, or a range from about 10 µg/kg of body weight to about 20 mg/cm$^2$, or a range from about 50 µg/kg of body weight to about 10 mg/cm$^2$, or a range from about 200 µg/kg of body weight to about 5 mg/cm$^2$.

The Examples set forth herein below are illustrative of certain embodiments of the present invention and are not intended to limit, in any way, the full scope of the present invention.

EXAMPLES

Example 1

Preparation—Carvedilol Dihydrogen Phosphate Hemihydrate

Reactor was charged with 252 ml acetone, 28 g. carvedilol and 30 ml water. Cooled the contents to 0-5° C. Charged 5 g. phosphorus pentaoxide at 0-5° C. The temperature was raised to 40-45° C., maintained for 60 minutes. The contents were cooled to 0-5° C. The solid precipitate formed was stirred at 0-5° C., then filtered and washed with aqueous acetone. The cake was dried under vacuum to a constant weight.

Yield: 95%, purity 99.7%

Preparation—Carvedilol Dihydrogen Phosphate Monohydrate

The reactor was charged with 20 g (0.039 M) carvedilol phosphate hemihydrate and 250 ml (13.9M) water. The contents of the reaction mass were heated to 50-55° C. for 30 minutes. Acetone (200 ml, 2.75 M) was added to reaction mass at 50-55° C. and maintained for 60 minutes. Reaction mass was cooled to 30-35° C. and stirred for 24 hours. Reaction mass was subjected to vacuum distillation to distill out acetone. Reaction mass was cooled to 5-10° C., filtered and washed with water. Carvedilol dihydrogen phosphate monohydrate was dried at 40-45° C. till constant weight.

Yield: 85-90%, HPLC purity—99.8%, moisture content 3-4%.

Example 2

Reactor was charged with carvedilol (10 gm, 0.025M) and water (160 ml, 8.89M). Contents were stirred at 30-35° C. for 15 minutes. To reaction mass was added phosphoric acid (3.5 gm, 85% purity, 0.036M) and contents were stirred at 30-35° C. for 30 minutes. To the reaction mixture, acetone (35 ml, 0.48M) was added and further maintained at 30-35° C. for 24 hours. Reaction mixture was cooled to ~5-10° C. and carvedilol dihydrogen phosphate monohydrate formed was filtered and washed with water, suck dried and dried under vacuum at ~45° C. till constant weight.

Yield: 90-95%. HPLC Purity: 99.8%, moisture content 3-4%

Example 3

Carvedilol (10 gm) (0.025M) was suspended in water (120 ml, 6.66M) and stirred at 30-35° C. for 10 minutes. To the reaction mass was added phosphoric acid (3.5 gm, 85% purity, 0.036M) and stirred at 30-35° C. for half an hour. Reaction mass was stirred at 55° C. for half an hour and isopropyl alcohol (80 ml, 1.067M) was added and contents were stirred at ~55° C. for 1 hour. Reaction mass was cooled to 30-35° C. and stirred for 24 hours. Contents were further cooled to 5-10° C. and maintained for 1 hour. Carvedilol dihydrogen phosphate monohydrate was filtered and washed with water, suck dried and dried under vacuum at ~45° C. till constant weight.

Yield: 85-90%, HPLC Purity: 99.9%, moisture content 3-4%

Example 4

Reactor was charged with carvedilol (10 gm, 0.025M) and water (160 ml, 8.8 M). Contents were stirred at 30-35° C. for 15 minutes. To the reaction mass was added phosphorus pentaoxide (4 gm, 0.035 M). Reaction mass was heated to 50-55° C. and acetone (35 ml, 0.5M) was added. Contents were stirred at 50-55° C. for two hours, cooled to 30-35° C. and stirred for 24 hours. Contents were cooled to 5-10° C. and carvedilol dihydrogen phosphate monohydrate formed was filtered, washed with water, suck dried and dried under vacuum at ~45° C. till constant weight.

Yield: 85-90%, HPLC Purity: 99.8%, moisture content 3-4%

Example 5

Carvedilol (15 gm, 0.0375M), water (240 ml, 13.33M) and dipotassium hydrogen orthophosphate (6.5 g, 0.0375M) were charged in to a reactor and stirred for 10 minutes at 30-35° C. Cooled the reaction mass to 5-10° C. The pH of the reaction mass was adjusted to 4.5-5 with hydrochloric acid. The temperature was raised to 50-55° C. Acetone (51 ml, 0.7M) was added and stirred at 50-55° C. for two hours. Reaction mass was cooled to 30-35° C. and stirred for 24 hours. The reaction mass was further cooled to 5-10° C. and maintained for 1 hour. Carvedilol dihydrogen phosphate monohydrate was filtered, washed with water, suck dried and dried under vacuum at 40-45° C. till constant weight to obtain carvedilol phosphate monohydrate.

Yield: 87%, Purity—99.4%, moisture content 3-4%

Example 6

Carvedilol (15 gm, 0.0375M), water (240 ml, 13.33 M) and polyphosphoric acid (3.7 g) were charged in to a reactor and stirred for 10 minutes at 30-35° C. The reaction mass was cooled to 5-10° C. The pH of the reaction mass was adjusted to 4.5-5 with hydrochloric acid. The temperature was raised to 50-55° C. Acetone (51 ml, 0.7 M) was added and stirred at 50-55° C. for 2 hours. Reaction mass was cooled to 30-35° C. and stirred for 24 hours. The reaction mass was further cooled to 5-10° C. and maintained for 1 hour. Carvedilol dihydrogen phosphate monohydrate was filtered, washed with water, suck dried and dried under vacuum at 40-45° C. till constant weight.

Yield: 91%, Purity—99.6%, moisture content 3-4%

Example 7

The carvedilol dihydrogen phosphate monohydrate product prepared by methods such as those presented in Examples 1-6 as well as similar methods as generally described herein has been further characterized by x-ray diffraction, differential scanning calorimetry (DSC), and IR and NMR spectroscopy.

The x-ray diffraction pattern for carvedilol dihydrogen phosphate monohydrate (FIG. 1) depicts characteristic peaks in degrees two-theta (2 θ) values. Observed values for degrees two-theta for major peaks and several minor peaks are transcribed from FIG. 1 in Table 1.

TABLE 1

X-ray diffraction peak positions

| Peaks [°2-Theta] | Peaks[°2-Theta] |
|---|---|
| 5.460 | 17.640 |
| 6.413 | 18.205 |
| 6.658 | 18.827 |
| 6.949 | 19.349 |
| 7.949 | 19.653 |
| 9.118 | 20.610 |
| 9.628 | 22.105 |
| 11.3 | 22.786 |
| 12.547 | 23.091 |
| 12.858 | 23.952 |
| 13.386 | 24.566 |
| 13.904 | 25.060 |
| 14.304 | 25.321 |
| 14.739 | 27.078 |
| 15.370 | 27.838 |
| 15.924 | 28.220 |
| 16.168 | 30.668 |
| 16.812 | |

Figure 2:
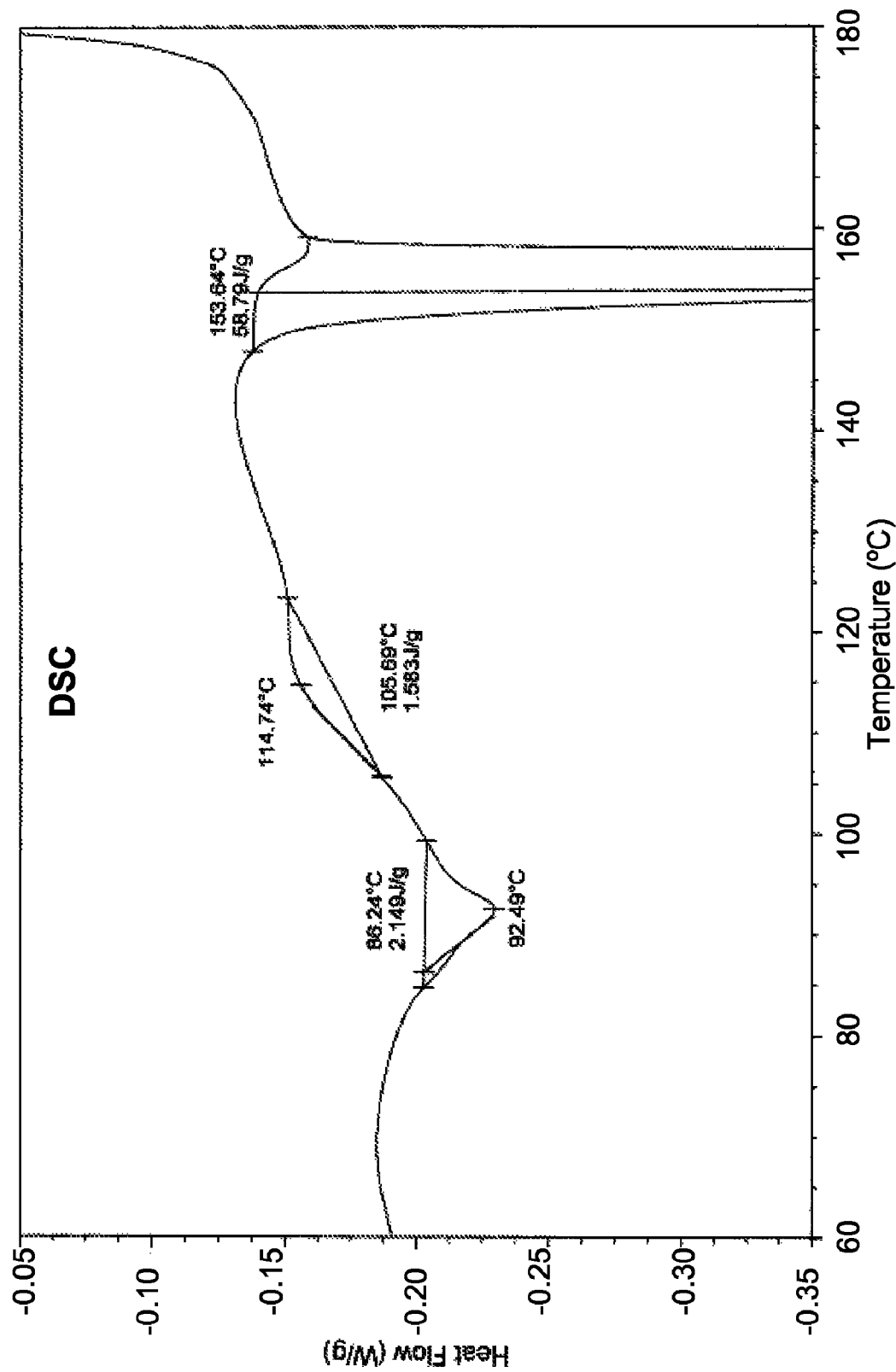
FIG. 2 presents a differential scanning calorimetric thermogram for carvedilol dihydrogen phosphate monohydrate.

The DSC thermogram shown in FIG. 2 includes three characteristic peaks. The first peak is an endothermic peak whose envelop is extrapolated as occurring at a temperature ranging from about 84.7° C. to about 99.3° C. The first peak is attributed to loss of one mole of water, confirming that the product is the monohydrate of carvedilol phosphate.

A second peak is an exothermic peak whose envelop is extrapolated as occurring at a temperature range of about 105.5° C. to about 123.4° C. This peak is ascribed to an exothermic transition in the structure of the crystal from that of the hydrated compound to the anhydrous compound after the loss of the monohydrate's water of hydration.

The third peak is an endothermic peak whose envelop is extrapolated as occurring at an onset temperature of about 156±3° C., which corresponds to the melting point of the product.

Figure 3:
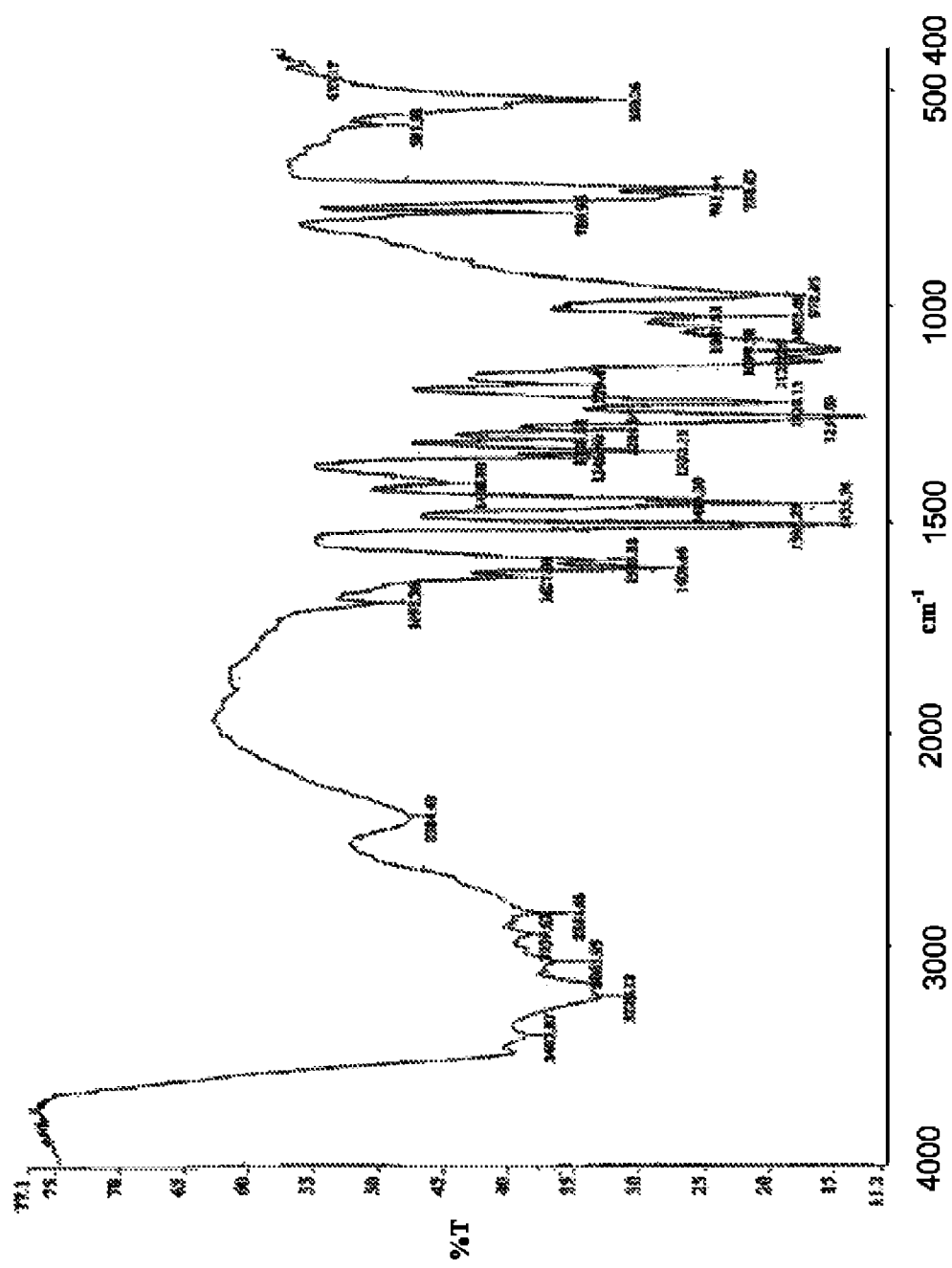
FIG. 3 presents an FTIR spectrum for carvedilol dihydrogen phosphate monohydrate.

The FTIR spectrum of carvedilol dihydrogen phosphate monohydrate is shown in FIG. 3. Positions of peaks in the spectrum are transcribed from FIG. 3 in Table 2.

TABLE 2

FTIR Band positions

| ν, cm$^{-1}$ | ν, cm$^{-1}$ |
|---|---|
| 433.17 | 1332.75 |
| 520.26 | 1346.40 |
| 581.91 | 1408.80 |
| 728.03 | 1443.30 |
| 741.94 | 1455.74 |
| 786.96 | 1505.27 |
| 972.65 | 1586.88 |
| 1022.09 | 1606.66 |
| 1047.53 | 1627.01 |
| 1099.30 | 1691.36 |
| 1126.26 | 2384.49 |
| 1179.47 | 2841.86 |
| 1220.13 | 2939.62 |
| 1254.03 | 3065.95 |

TABLE 2-continued

FTIR Band positions

| ν, cm$^{-1}$ | ν, cm$^{-1}$ |
|---|---|
| 1284.07 | 3229.17 |
| 1305.51 | 3407.87 |

Figure 4:
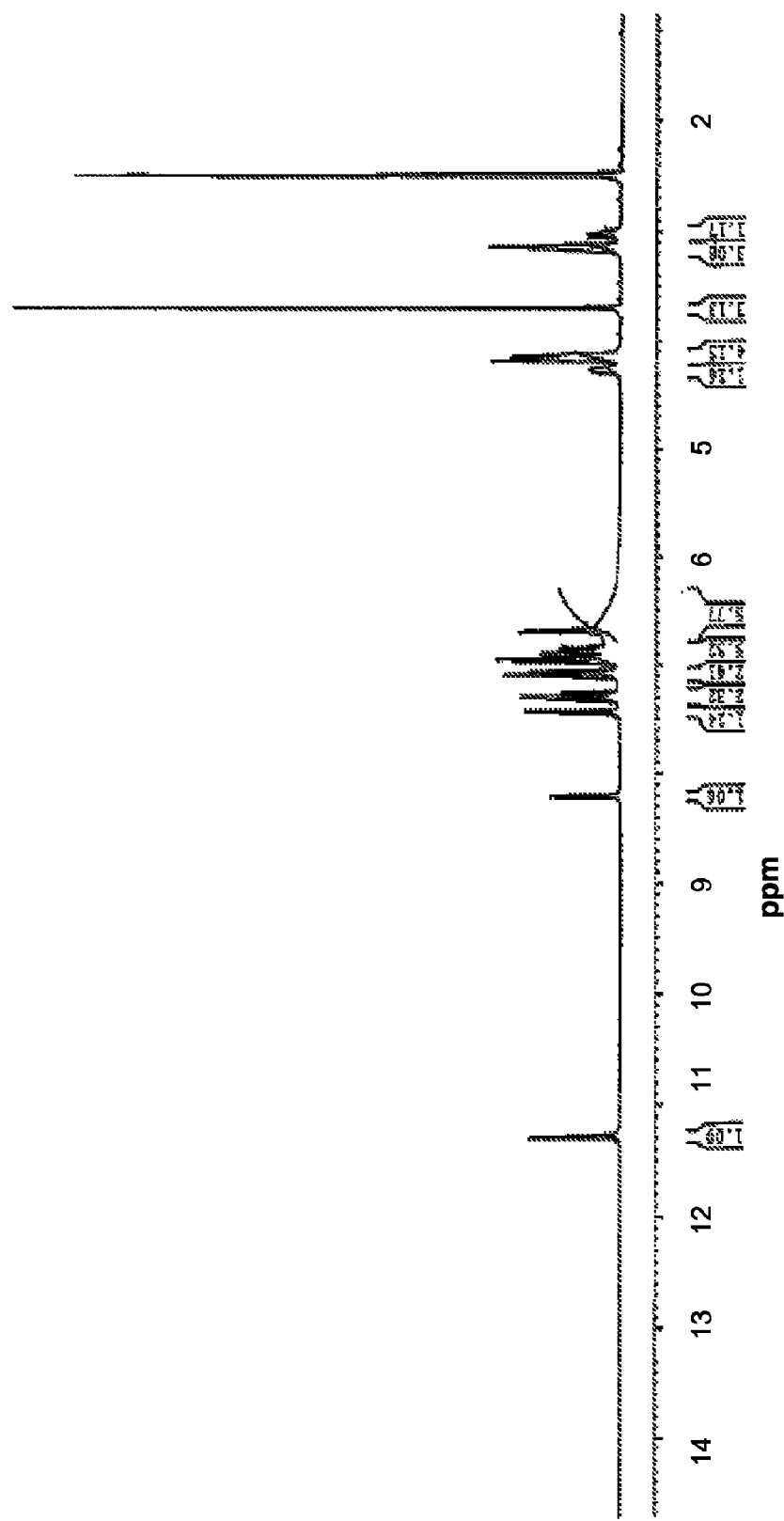
FIG. 4 presents a $^1$H NMR spectrum for carvedilol dihydrogen phosphate monohydrate.

The $^1$H NMR spectrum of carvedilol phosphate monohydrate prepared by methods such as those disclosed herein is presented in FIG. 4. It includes the following characteristic peaks as shown in Table 3, using the individual proton designations given in Structure III.

TABLE 3

III

| Chemical shift, ppm | No. of Proton | Assigned proton | Splitting pattern |
|---|---|---|---|
| 2.5 | | DMSO | |
| 2.9-3.3 | 4 | e & g | Multiplet |
| 3.7 | 3 | a | Singlet |
| 4.0-4.2 | 4 | d & j | Multiplet |
| 4.2-4.3 | 1 | h | Multiplet |
| 6.4-6.7 | 5 | H$_2$O & H$_3$PO$_4$ | Doublet |
| 6.8-7.5 | 11 | b, c, k, l, m, o, p, q, r | Aromatic multiplet |
| 8.2-8.3 | 1 | i | doublet |
| 11.2-11.4 | 1 | n | Singlet |

The doublet at 6.4-6.7 ppm has an amplitude corresponding to 5 protons, ascribed to the total number of protons in the water of hydration and the phosphoric acid protons. This is consistent with the product being the monohydrate of carvedilol phosphate.

Example 8

The dissolution rate of carvedilol dihydrogen phosphate monohydrate as a capsule formulation was compared with that of carvedilol phosphate hemihydrate similarly prepared.

The samples for the dissolution study were prepared as follows:

Carvedilol phosphate, 25.0 mg, was accurately weighed along with lactose and other fillers. The mix was filled inside a colorless gelatin capsule shell, size #2. Six such capsules were subjected to dissolution studies, each for the monohydrate and hemi-hydrate material.

The intrinsic solubility of the monohydrate form versus the hemihydrate form of carvedilol is done using the general guidelines for characterizing the dissolution rate as per the United States Pharmacopoeia.

The dissolution conditions were:
Apparatus: USP Type 1
Medium: 0.1 N hydrochloric acid, 900 ml
Speed of rotations: 100 per minute.
Temp: 37 degree±0.05 degrees.
Time points: 10, 20, 30, 45, 60 and 90 minutes.
The percent dissolved: was determined by UV spectrophotometry at a wavelength of 280 nm.

The results of the dissolution study are described below in table 4:

TABLE 4

| Time | % Dissolved | |
|---|---|---|
| | Hemihydrate form | Monohydrate form |
| 10 min | 45.95 | 46.20 |
| 20 min | 63.75 | 68.28 |
| 30 min | 68.43 | 82.45 |
| 45 min | 75.99 | 95.89 |
| 60 min | 82.68 | 96.81 |
| 90 min | 88.95 | 101.55 |

Under the conditions studied, the monohydrate form of carvedilol dihydrogen phosphate has a faster rate of dissolution than the hemihydrate form. Complete dissolution of carvedilol phosphate monohydrate is observed within 90 minutes, compared to less than 90% for the hemihydrate form at the same time. This unexpected result shows that carvedilol phosphate monohydrate has more advantageous pharmaceutical properties than a known carvedilol phosphate composition. Specifically, this result suggests that carvedilol phosphate monohydrate administered orally becomes bioavailable more rapidly than a known carvedilol phosphate composition.

It is to be understood that the invention is not limited to the embodiments illustrated here in above and the right is reserved to the illustrated embodiments and all modifications coming within the scope of the following claims.

We claim:

1. Crystalline carvedilol dihydrogen phosphate monohydrate.

2. The carvedilol dihydrogen phosphate monohydrate according to claim 1 characterized by X-ray diffraction pattern having characteristic peaks in degrees two-theta (2 θ) values at about 6.95±0.2 (2 θ), 15.92±0.2 (2 θ), 17.64±0.2 (2 θ), 18.83±0.2 (2 θ), 20.60±0.2 (2 θ), 22.78±0.2 (2 θ), 24.57±0.2 (2 θ), and 25.32±0.2 (2 θ).

3. The carvedilol dihydrogen phosphate monohydrate according to claim 1 characterized by a differential scanning calorimetry thermogram having a first endothermic peak extending from about 84.7° C. to about 99.3° C.; a second exothermic peak extending from about 105.5° C. to 123.37° C. and a third endothermic peak at an extrapolated onset temperature of 156±3° C.

4. The carvedilol dihydrogen phosphate monohydrate according to claim 1 wherein the water content is between 3.0 to 4.0% by weight.

5. A process for preparation of carvedilol dihydrogen phosphate monohydrate in high yield comprising the steps of:
a. preparing a slurry of carvedilol in water;
b. contacting the slurried carvedilol with a composition comprising a source of phosphate at a temperature from about 25 to about 55° C., thereby generating a phosphate salt of carvedilol in water;
c. adding a water-miscible organic solvent to the aqueous carvedilol phosphate salt at a temperature from about 25 to about 55° C.; and
d. cooling the aqueous-organic mixture and isolating solid carvedilol dihydrogen phosphate monohydrate salt from the mixture.

6. The process as claimed in claim 5, wherein the source of phosphate is selected from the group consisting of phosphoric acid, phosphorus pentoxide, polyphosphoric acid, dipotassium hydrogen phosphate, ammonium dihydrogen ortho phosphate, sodium dihydrogen ortho phosphate, and a mixture of any two or more of them.

7. The process as claimed in claim 5, wherein the source of phosphate comprises phosphoric acid.

8. The process as claimed in claim 5, wherein the source of phosphate comprises phosphorus pentoxide.

9. The process as claimed in claim 5, wherein the source of phosphate comprises polyphosphoric acid.

10. The process as claimed in claim 5, wherein the source of phosphate comprises dipotassium hydrogen phosphate.

11. The process as claimed in claim 5, wherein the source of phosphate comprises ammonium dihydrogen ortho phosphate.

12. The process as claimed in claim 5, wherein the source of phosphate comprises sodium dihydrogen ortho phosphate and hydrochloric acid.

13. The process as claimed in claim 5 wherein the organic solvent comprises acetonitrile, tetrahydrofuran, dioxane, ethanol, n-propanol, isopropanol, or acetone, or a mixture of two or more of them.

14. The process as claimed in claim 13, wherein said solvent comprises acetonitrile.

15. The process as claimed in claim 13, wherein said solvent comprises tetrahydrofuran.

16. The process as claimed in claim 13, wherein said solvent comprises acetone.

17. The process as claimed in claim 13, wherein said solvent comprises isopropyl alcohol.

18. The process as claimed in claim 5 wherein the ratio of water:organic solvent, expressed as volume:volume, ranges from 1:1 to 5:1.

19. A pharmaceutical composition comprising carvedilol dihydrogen phosphate monohydrate and a pharmaceutical carrier.

20. A method for treating a cardiovascular disease in a mammal, wherein the method comprises administering to the mammal a therapeutically effective amount of a pharmaceutical composition comprising carvedilol dihydrogen phosphate monohydrate.

21. The method as claimed in claim 20 wherein the cardiovascular disease is one or more of hypertension, congestive heart failure and angina.

22. The method as claimed in claim 20 wherein the mammal is a human.

23. A method of preparing a pharmaceutical composition for treating a cardiovascular disease in a mammal, comprising combining crystalline carvedilol dihydrogen phosphate monohydrate and a pharmaceutical acceptable carrier.

24. The method as claimed in claim 23 wherein the pharmaceutical composition is suitable for oral administration.

* * * * *